United States Patent
Himmelsbach et al.

(10) Patent No.: US 7,495,005 B2
(45) Date of Patent: Feb. 24, 2009

(54) XANTHINE DERIVATIVES, THEIR PREPARATION AND THEIR USE IN PHARMACEUTICAL COMPOSITIONS

(75) Inventors: Frank Himmelsbach, Mittelbiberach (DE); Elke Langkopf, Warthausen (DE); Matthias Eckhardt, Biberach (DE); Michael Mark, Biberach (DE); Roland Maier, Biberach an der Riss (DE); Ralf R. H. Lotz, Schemmerhofen (DE)

(73) Assignee: Boehringer Ingelheim Pharma GmbH & Co. KG, Ingelheim (DE)

(*) Notice: Subject to any disclaimer, the term of this patent is extended or adjusted under 35 U.S.C. 154(b) by 0 days.

(21) Appl. No.: 10/636,088

(22) Filed: Aug. 7, 2003

(65) Prior Publication Data

US 2004/0166125 A1 Aug. 26, 2004

Related U.S. Application Data

(60) Provisional application No. 60/409,258, filed on Sep. 9, 2002.

(30) Foreign Application Priority Data

Aug. 22, 2002 (DE) ............................... 102 38 470

(51) Int. Cl.
C07D 473/06 (2006.01)
A61K 31/522 (2006.01)
A61P 3/10 (2006.01)

(52) U.S. Cl. .................. 514/263.22; 544/118; 544/268; 544/269; 544/270; 544/271

(58) Field of Classification Search ................ 544/118, 544/268, 269, 270, 271; 514/234.2, 263.2, 514/263.21, 263.22, 263.23, 263.35, 263.34
See application file for complete search history.

(56) References Cited

U.S. PATENT DOCUMENTS

| | | | |
|---|---|---|---|
| 2,928,833 A | 3/1960 | Leake et al. | |
| 4,005,208 A | 1/1977 | Bender | |
| 4,599,338 A | 7/1986 | Regnier et al. | |
| 5,041,448 A | 8/1991 | Janssens | |
| 5,051,517 A | 9/1991 | Findeisen | |
| 5,223,499 A | 6/1993 | Greenlee | |
| 5,234,897 A | 8/1993 | Findeisen et al. | |
| 5,258,380 A | 11/1993 | Janssens | |
| 5,266,555 A | 11/1993 | Findeisen et al. | |
| 5,389,642 A | 2/1995 | Dorsch | |
| 5,470,579 A | 11/1995 | Bonte et al. | |
| 5,719,279 A | 2/1998 | Kuefner-Muhl et al. | |
| 5,753,635 A | 5/1998 | Buckman | |
| 6,303,661 B1 | 10/2001 | Demuth | |
| 6,342,601 B1 | 1/2002 | Bantick | |
| 6,548,481 B1 | 4/2003 | Demuth et al. | |
| 6,579,868 B1 | 6/2003 | Asano | |
| 6,821,978 B2 | 11/2004 | Chackalamannil | |
| 6,869,947 B2 | 3/2005 | Kanstrup | |
| 7,060,722 B2 | 6/2006 | Kitajima | |
| 7,074,794 B2 | 7/2006 | Kitajima | |
| 7,074,798 B2 | 7/2006 | Yoshikawa | |
| 7,074,923 B2 | 7/2006 | Dahanukar | |
| 7,109,192 B2 | 9/2006 | Hauel | |
| 7,179,809 B2 | 2/2007 | Eckhardt | |
| 7,183,280 B2 | 2/2007 | Himmelsbach | |
| 7,192,952 B2 | 3/2007 | Kanstrup | |
| 7,217,711 B2 | 5/2007 | Eckhardt | |
| 7,235,538 B2 | 6/2007 | Kanstrup et al. | |
| 2002/0161001 A1 | 10/2002 | Kanstrup et al. | |
| 2002/0169174 A1 | 11/2002 | Chackalamannil et al. | |
| 2002/0198205 A1 | 12/2002 | Himmelsbach et al. | |
| 2003/0105077 A1 | 6/2003 | Kanstrup et al. | |
| 2003/0199528 A1 | 10/2003 | Kanstrup et al. | |
| 2003/0232987 A1 | 12/2003 | Dahanukar et al. | |
| 2003/0236272 A1 | 12/2003 | Carr | |
| 2004/0034014 A1 | 2/2004 | Kanstrup et al. | |
| 2004/0077645 A1* | 4/2004 | Himmelsbach et al. | .. 514/234.5 |
| 2004/0082570 A1 | 4/2004 | Yoshikawa | |
| 2004/0087587 A1* | 5/2004 | Himmelsbach et al. | .. 514/234.5 |
| 2004/0097510 A1* | 5/2004 | Himmelsbach et al. | ..... 514/248 |

(Continued)

FOREIGN PATENT DOCUMENTS

CA 2136288 A1 5/1995

(Continued)

OTHER PUBLICATIONS

Busso et al., American Journal of Pathology 166:433-442 (2005).*

(Continued)

*Primary Examiner*—Mark L Berch
(74) *Attorney, Agent, or Firm*—Michael P. Morris; Mary-Ellen M. Devlin; David L. Kershner

(57) ABSTRACT

Compounds of formula (I)

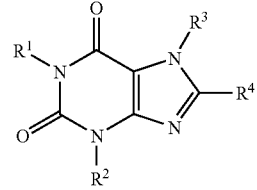

(I)

wherein $R^1$ is a phenylcarbonylmethyl group wherein the phenyl moiety is substituted, and $R^2$ to $R^4$ are defined as in the claims, or the prodrugs or salts thereof, particularly the physiologically acceptable salts thereof, pharmaceutical compositions containing these compounds, and methods of treating type I and type II diabetes mellitus, arthritis, obesity, allograft transplantation and calcitonin-induced osteoporosis using these compounds.

10 Claims, No Drawings

U.S. PATENT DOCUMENTS

| | | |
|---|---|---|
| 2004/0116328 A1 | 6/2004 | Yoshikawa et al. |
| 2004/0122228 A1* | 6/2004 | Maier et al. .................. 544/117 |
| 2004/0138214 A1* | 7/2004 | Himmelsbach et al. .. 514/230.5 |
| 2004/0138215 A1* | 7/2004 | Eckhardt et al. ......... 514/234.5 |
| 2005/0020574 A1 | 1/2005 | Hauel et al. |
| 2005/0026921 A1 | 2/2005 | Eckhardt |
| 2005/0130985 A1 | 6/2005 | Himmelsbach |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt |
| 2005/0234108 A1 | 10/2005 | Himmelsbach et al. |
| 2005/0261352 A1 | 11/2005 | Eckhardt |
| 2006/0004074 A1 | 1/2006 | Eckhardt |
| 2006/0058323 A1 | 3/2006 | Eckhardt et al. |
| 2006/0063787 A1* | 3/2006 | Yoshikawa et al. ........ 514/263.2 |
| 2006/0079541 A1* | 4/2006 | Langkopf et al. ...... 514/263.35 |
| 2006/0094722 A1 | 5/2006 | Yasuda |
| 2006/0142310 A1 | 6/2006 | Pfrengle et al. |
| 2006/0173056 A1 | 8/2006 | Kitajima |
| 2006/0205711 A1 | 9/2006 | Himmelsbach |
| 2006/0247226 A1 | 11/2006 | Himmelsbach |
| 2007/0027168 A1 | 2/2007 | Pfrengle et al. |
| 2007/0088038 A1 | 4/2007 | Eckhardt |
| 2007/0093659 A1 | 4/2007 | Bonfanti |
| 2007/0142383 A1 | 6/2007 | Eckhardt |
| 2007/0185091 A1 | 8/2007 | Himmelsbach et al. |
| 2007/0219178 A1 | 9/2007 | Muramoto |
| 2007/0259900 A1 | 11/2007 | Sieger |
| 2007/0281940 A1 | 12/2007 | Dugi |

FOREIGN PATENT DOCUMENTS

| | | | |
|---|---|---|---|
| CA | 2418656 | A1 | 2/2002 |
| CA | 2496325 | A1 | 3/2004 |
| CA | 2496249 | A1 | 4/2004 |
| CA | 2505389 | A1 | 5/2004 |
| CA | 2508233 | A1 | 6/2004 |
| CA | 2529729 | A1 | 12/2004 |
| CA | 2543074 | A1 | 6/2005 |
| CA | 2555050 | A1 | 9/2005 |
| CA | 2556064 | A1 | 9/2005 |
| CA | 2590912 | A1 | 6/2006 |
| DE | 10109021 | A1 | 9/2002 |
| DE | 10117803 | A1 | 10/2002 |
| EP | 0149578 | A2 | 7/1985 |
| EP | 0400974 | A2 | 5/1990 |
| EP | 0399285 | A1 | 11/1990 |
| EP | 0412358 | A1 | 2/1991 |
| EP | 0524482 | A1 | 1/1993 |
| EP | 0657454 | A1 | 6/1995 |
| EP | 1054012 | A1 | 11/2000 |
| EP | 1 338 595 | A2 | 8/2003 |
| EP | 1338595 | A2 | 8/2003 |
| EP | 1514552 | A1 | 3/2005 |
| EP | 1537880 | A1 | 8/2005 |
| ES | 385302 | A1 | 4/1973 |
| FR | 2707641 | A1 | 1/1995 |
| JP | S37-4895 | | 6/1962 |
| JP | 2003/300977 | | 10/2003 |
| JP | 2006/045156 | | 2/2006 |
| WO | 91/07945 | A1 | 6/1991 |
| WO | 94/03456 | A1 | 2/1994 |
| WO | 99/29695 | A1 | 6/1999 |
| WO | 02/02560 | A2 | 1/2002 |
| WO | WO 02/02560 | A2 | 1/2002 |
| WO | 02/14271 | A1 | 2/2002 |
| WO | 02/24698 | A1 | 3/2002 |
| WO | 02/068420 | A1 | 9/2002 |
| WO | WO 02/068420 | A1 | 9/2002 |
| WO | 03/004496 | A1 | 1/2003 |
| WO | WO 03/004496 | A1 | 1/2003 |
| WO | 03/024965 | A2 | 3/2003 |
| WO | WO 03/024965 | A2 | 3/2003 |
| WO | WO 03/057200 | A2 | 7/2003 |
| WO | 03/104229 | A1 | 12/2003 |
| WO | 2004/018467 | A2 | 3/2004 |
| WO | 2004/018468 | A2 | 3/2004 |
| WO | 2004/028524 | A1 | 4/2004 |
| WO | 2004/033455 | A2 | 4/2004 |
| WO | 2004/041820 | A1 | 5/2004 |
| WO | 2004/046148 | A1 | 6/2004 |
| WO | 2004/048379 | A1 | 6/2004 |
| WO | 2004/050658 | A1 | 6/2004 |
| WO | 2004/096806 | A1 | 11/2004 |
| WO | 2004/108730 | A1 | 12/2004 |
| WO | 2004/111051 | A1 | 12/2004 |
| WO | 2005/058901 | A1 | 6/2005 |
| WO | 2005/082906 | A1 | 9/2005 |
| WO | 2005/085246 | A1 | 9/2005 |
| WO | 2006/029769 | A1 | 3/2006 |
| WO | 2006/048427 | A1 | 5/2006 |
| WO | 2006/068163 | A1 | 6/2006 |
| WO | 2007/017423 | A2 | 2/2007 |

OTHER PUBLICATIONS

Januvia; Patient Information; Oct. 2007.

U.S. Appl. No. 11/744,701, filed May 4, 2007, Kohlrausch.

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors, (2003).

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

* cited by examiner

XANTHINE DERIVATIVES, THEIR PREPARATION AND THEIR USE IN PHARMACEUTICAL COMPOSITIONS

RELATED APPLICATIONS

This application claims priority to U.S. Serial No. 60/409,258, filed Sep. 9, 2002, and German Application No. 102 38 470.3, filed Aug. 22, 2002, each of which is hereby incorporated by reference in its entirety.

SUMMARY OF THE INVENTION

The present invention relates to new substituted xanthines of general formula (I)

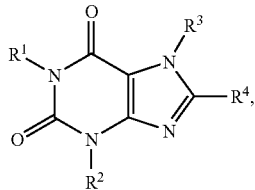

the tautomers, enantiomers, diastereomers, the mixtures thereof, the prodrugs thereof and the salts thereof, particularly the physiologically acceptable salts thereof with inorganic or organic acids or bases which have valuable pharmacological properties, particularly an inhibiting effect on the activity of the enzyme dipeptidylpeptidase-IV (DPP-IV), the preparation thereof, the use thereof for the prevention or treatment of diseases or conditions associated with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof as well as processes for the preparation thereof.

In the above formula (I):

$R^1$ denotes a phenylcarbonylmethyl group wherein the phenyl moiety is substituted by $R^{10}$ and $R^{11}$, wherein:
  $R^{10}$ denotes a formylamino group,
    a $C_{3-7}$-cycloalkyl-carbonylamino or $C_{3-7}$-cycloalkyl-$C_{1-3}$-alkyl-carbonylamino group,
    a $C_{6-9}$-bicycloalkyl-carbonylamino or $C_{6-9}$-bicycloalkyl-$C_{1-3}$-alkyl-carbonylamino group,
    a $C_{5-7}$-cycloalkyl-carbonylamino group wherein a methylene group is replaced by an oxygen or sulfur atom or by an imino, sulfinyl, or sulfonyl group,
    a $C_{5-7}$-cycloalkyl-carbonylamino group wherein a —$CH_2$—$CH_2$ group is replaced by a —NH—CO or —NH—NH group,
    a $C_{5-7}$-cycloalkyl-carbonylamino group wherein a —$CH_2$—$CH_2$—$CH_2$ group is replaced by a —NH—CO—NH, —NH—CO—O, or —O—$CH_2$—O group,
    a $C_{6-7}$-cycloalkyl-carbonylamino group wherein a —$CH_2$—$CH_2$—$CH_2$—$CH_2$ group is replaced by a —NH—$CH_2$—$CH_2$—NH, —NH—CO—$CH_2$—H, —NH—$CH_2$—$CH_2$—O, —NH—CO—$CH_2$—O, or —O—$CH_2$—$CH_2$—O group,
    a cycloheptyl-carbonylamino group wherein a —$CH_2$—$CH_2$—$CH_2$—$CH_2$ group is replaced by a —NH—$CH_2$—$CH_2$—$CH_2$—NH, —NH—CO—$CH_2$—$CH_2$—NH, —NH—$CH_2$—$CH_2$—$CH_2$—O, —NH—CO—$CH_2$—$CH_2$—O, or —O—$CH_2$—$CH_2$—$CH_2$—O group,
    a $C_{5-7}$-cycloalkyl-carbonylamino group wherein one or two methylene groups are replaced by carbonyl groups,
    a $C_{4-7}$-cycloalkenyl-carbonylamino or $C_{4-7}$-cycloalkenyl-$C_{1-3}$-alkyl-carbonylamino group,
    a $C_{3-7}$-cycloalkyl-sulfonylamino, $C_{3-7}$-cycloalkyl-$C_{1-3}$-alkyl-sulfonylamino, arylsulfonylamino, or aryl-$C_{1-3}$-alkyl-sulfonylamino group or
    a heteroarylcarbonylamino group,
    wherein the imino groups contained in the abovementioned groups may be substituted independently of one another by a $C_{1-3}$-alkyl group, and
  $R^{11}$ denotes a hydrogen, fluorine, chlorine, bromine, or iodine atom or a $C_{1-3}$-alkyl, $C_{1-3}$-alkyloxy, difluoromethyl, trifluoromethyl, difluoromethoxy, trifluoromethoxy, or cyano group;

$R^2$ denotes a hydrogen atom,
  a $C_{1-6}$-alkyl group,
  a $C_{2-4}$-alkenyl group,
  a $C_{3-4}$-alkynyl group,
  a $C_{3-6}$-cycloalkyl group,
  a $C_{3-6}$-cycloalkyl-$C_{1-3}$-alkyl group,
  a tetrahydrofuran-3-yl, tetrahydropyran-3-yl, tetrahydropyran-4-yl, tetrahydrofuranylmethyl, or tetrahydropyranylmethyl group,
  an aryl group,
  an aryl-$C_{1-4}$-alkyl group,
  an aryl-$C_{2-3}$-alkenyl group,
  an arylcarbonyl-$C_{1-2}$-alkyl group,
  a heteroaryl-$C_{1-3}$-alkyl group,
  a furanylcarbonylmethyl, thienylcarbonylmethyl, thiazolylcarbonylmethyl, or pyridylcarbonylmethyl group,
  a $C_{1-4}$-alkyl-carbonyl-$C_{1-2}$-alkyl group,
  a $C_{3-6}$-cycloalkyl-carbonyl-$C_{1-2}$-alkyl group,
  an aryl-D-$C_{1-3}$-alkyl group, while D denotes an oxygen or sulfur atom, an imino, $C_{1-3}$-alkylimino, sulfinyl, or sulfonyl group,
  a $C_{1-4}$-alkyl group substituted by a group $R_a$, wherein $R_a$ denotes a cyano, carboxy, $C_{1-3}$-alkyloxy-carbonyl, aminocarbonyl, $C_{1-3}$-alkylamino-carbonyl, di-($C_{1-3}$-alkyl)-aminocarbonyl, pyrrolidin-1-ylcarbonyl, piperidin-1-ylcarbonyl, morpholin-4-ylcarbonyl, piperazin-1-ylcarbonyl, 4-methylpiperazin-1-ylcarbonyl, or 4-ethylpiperazin-1-ylcarbonyl group, or
  a $C_{2-4}$-alkyl group substituted by a group $R_b$, wherein $R_b$ denotes a hydroxy, $C_{1-3}$-alkyloxy, amino, $C_{1-3}$-alkylamino, di-($C_{1-3}$-alkyl)-amino, pyrrolidin-1-yl, piperidin-1-yl, morpholin-4-yl, piperazin-1-yl, 4-methylpiperazin-1-yl, or 4-ethylpiperazin-1-yl group and is isolated from the cyclic nitrogen atom in the 3 position of the xanthine skeleton by at least two carbon atoms;

$R^3$ denotes a $C_{3-8}$-alkyl group,
  a $C_{1-3}$-alkyl group substituted by a group $R_c$, wherein:
    $R_c$ denotes a $C_{3-7}$-cycloalkyl group optionally substituted by one or two $C_{1-3}$-alkyl groups,
    a $C_{5-7}$-cycloalkenyl group optionally substituted by one or two $C_{1-3}$-alkyl groups,
    an aryl group, or
    a furanyl, thienyl, oxazolyl, isoxazolyl, thiazolyl, isothiazolyl, pyridyl, pyridazinyl, pyrimidyl or pyrazinyl group, wherein the abovementioned heterocyclic groups may each be substituted by one or two $C_{1-3}$-alkyl groups or by a fluorine, chlorine, bromine, or iodine atom or by a trifluoromethyl, cyano, or $C_{1-3}$-alkyloxy group, a $C_{3-8}$-alkenyl group, a $C_{3-6}$-alkenyl group substituted by a fluorine, chlorine, or bromine atom, or a trifluoromethyl group, a $C_{3-8}$-alkynyl group, an aryl group, or an aryl-$C_{2-4}$-alkenyl group; and $R^4$ denotes an azetidin-1-yl or pyrrolidin-1-yl group which is substituted in the 3 position by an amino, $C_{1-3}$-alkylamino, or a di-($C_{1-3}$-alkyl)amino group and may additionally be substituted by one or two $C_{1-3}$-alkyl groups, a piperidin-1-yl or hexahydroazepin-1-yl group which is substituted in the 3 position or 4 position by an amino, $C_{1-3}$-alkylamino, or a di-($C_{1-3}$-alkyl)amino group and may additionally be substituted by one or two $C_{1-3}$-alkyl groups, a 3-aminopiperidin-1-yl group wherein the piperidin-1-yl moiety is additionally substituted by an aminocarbonyl, $C_{1-2}$-alkyl-aminocarbonyl, di-($C_{1-2}$-alkyl)aminocarbonyl, pyrrolidin-1-ylcarbonyl, (2-cyanopyrrolidin-1-yl)carbonyl, thiazolidin-3-ylcarbonyl, (4-cyanothiazolidin-3-yl)carbonyl, piperidin-1-ylcarbonyl, or morpholin-4-ylcarbonyl group, a 3-aminopiperidin-1-yl group wherein the piperidin-1-yl moiety is additionally substituted in the 4 position or 5 position by a hydroxy or methoxy group, a 3-aminopiperidin-1-yl group wherein the methylene group in the 2 position or 6 position is replaced by a carbonyl group, a piperidin-1-yl or hexahydroazepin-1-yl group substituted in the 3 position by an amino, $C_{1-3}$-alkylamino, or di-($C_{1-3}$-alkyl)-amino group, wherein in each case two hydrogen atoms on the carbon skeleton of the piperidin-1-yl or hexahydroazepin-1-yl group are replaced by a straight-chain alkylene bridge, this bridge containing 2 to 5 carbon atoms if the two hydrogen atoms are on the same carbon atom, or 1 to 4 carbon atoms if the hydrogen atoms are on adjacent carbon atoms, or 1 to 4 carbon atoms if the hydrogen atoms are on carbon atoms which are separated by one atom, or 1 to 3 carbon atoms if the hydrogen atoms are on carbon atoms which are separated by two atoms, an azetidin-1-yl, pyrrolidin-1-yl, piperidin-1-yl, or hexahydroazepin-1-yl group which is substituted by an amino-$C_{1-3}$-alkyl, $C_{1-3}$-alkylamino-$C_{1-3}$-alkyl, or a di-($C_{1-3}$-alkyl)amino-$C_{1-3}$-alkyl group, a piperazin-1-yl or [1,4]diazepan-1-yl group optionally substituted on the carbon skeleton by one or two $C_{1-3}$-alkyl groups, a 3-iminopiperazin-1-yl, 3-imino-[1,4]diazepan-1-yl, or 5-imino-[1,4]diazepan-1-yl group optionally substituted on the carbon skeleton by one or two $C_{1-3}$-alkyl groups, a [1,4]diazepan-1-yl group optionally substituted by one or two $C_{1-3}$-alkyl groups which is substituted in the 6 position by an amino group, a $C_{3-7}$-cycloalkyl group which is substituted by an amino, $C_{1-3}$-alkylamino, or di-($C_{1-3}$-alkyl)-amino group, a $C_{3-7}$-cycloalkyl group which is substituted by an amino-$C_{1-3}$-alkyl, $C_{1-3}$-alkylamino-$C_{1-3}$-alkyl, or a di-($C_{1-3}$-alkyl)amino-$C_{1-3}$-alkyl group, a $C_{3-7}$-cycloalkyl-$C_{1-2}$-alkyl group wherein the cycloalkyl moiety is substituted by an amino, $C_{1-3}$-alkylamino, or di-($C_{1-3}$-alkyl)-amino group, a $C_{3-7}$-cycloalkyl-$C_{1-2}$-alkyl group wherein the cycloalkyl moiety is substituted by an amino-$C_{1-3}$-alkyl, $C_{1-3}$-alkylamino-$C_{1-3}$-alkyl, or a di-($C_{1-3}$-alkyl)amino-$C_{1-3}$-alkyl group, a $C_{3-7}$-cycloalkylamino group wherein the cycloalkyl moiety is substituted by an amino, $C_{1-3}$-alkylamino, or di-($C_{1-3}$-alkyl)-amino group, while the two nitrogen atoms on the cycloalkyl moiety are separated from one another by at least two carbon atoms, an N—($C_{3-7}$-cycloalkyl)-N—($C_{1-3}$-alkyl)-amino group wherein the cycloalkyl moiety is substituted by an amino, $C_{1-3}$-alkylamino, or di-($C_{1-3}$-alkyl)-amino group, while the two nitrogen atoms on the cycloalkyl moiety are separated from one another by at least two carbon atoms, a $C_{3-7}$-cycloalkylamino group wherein the cycloalkyl moiety is substituted by an amino-$C_{1-3}$-alkyl, $C_{1-3}$-alkylamino-$C_{1-3}$-alkyl, or a di-($C_{1-3}$-alkyl)amino-$C_{1-3}$-alkyl group, an N—($C_{3-7}$-cycloalkyl)-N—($C_{1-3}$-alkyl)-amino group wherein the cycloalkyl moiety is substituted by an amino-$C_{1-3}$-alkyl, $C_{1-3}$-alkylamino-$C_{1-3}$-alkyl, or a di-($C_{1-3}$-alkyl)amino-$C_{1-3}$-alkyl group, a $C_{3-7}$-cycloalkyl-$C_{1-2}$-alkyl-amino group wherein the cycloalkyl moiety is substituted by an amino, $C_{1-3}$-alkylamino, or di-($C_{1-3}$-alkyl)-amino group, an N—($C_{3-7}$-cycloalkyl-$C_{1-2}$-alkyl)-N—($C_{1-2}$-alkyl)-amino group wherein the cycloalkyl moiety is substituted by an amino, $C_{1-3}$-alkylamino, or di-($C_{1-3}$-alkyl)-amino group, a $C_{3-7}$-cycloalkyl-$C_{1-2}$-alkyl-amino group wherein the cycloalkyl moiety is substituted by an amino-$C_{1-3}$-alkyl, $C_{1-3}$-alkylamino-$C_{1-3}$-alkyl, or a di-($C_{1-3}$-alkyl)amino-$C_{1-3}$-alkyl group, an N—($C_{3-7}$-cycloalkyl-$C_{1-2}$-alkyl)-N—($C_{1-2}$-alkyl)-amino group wherein the cycloalkyl moiety is substituted by an amino-$C_{1-3}$-alkyl, $C_{1-3}$-alkylamino-$C_{1-3}$-alkyl, or a di-($C_{1-3}$-alkyl)amino-$C_{1-3}$-alkyl group, an $R^{19}$—$C_{2-4}$-alkylamino group wherein $R^{19}$ is separated from the nitrogen atom of the $C_{2-4}$-alkylamino moiety by at least two carbon atoms and $R^{19}$ denotes an amino, $C_{1-3}$-alkylamino or di-($C_{1-3}$-alkyl)-amino group, an $R^{19}$—$C_{2-4}$-alkylamino group wherein the nitrogen atom of the $C_{2-4}$-alkylamino moiety is substituted by a $C_{1-3}$-alkyl group and $R^{19}$ is separated from the nitrogen atom of the $C_{2-4}$-alkylamino moiety by at least two carbon atoms, where $R^{19}$ is as hereinbefore defined, an amino group substituted by the group $R^{20}$ wherein $R^{20}$ denotes an azetidin-3-yl, azetidin-2-ylmethyl, azetidin-3-ylmethyl, pyrrolidin-3-yl, pyrrolidin-2-ylmethyl, pyrrolidin-3-ylmethyl, piperidin-3-yl, piperidin-4-yl, piperidin-2-ylmethyl, piperidin-3-ylmethyl, or piperidin-4-ylmethyl group, while the groups mentioned for $R^{20}$ may each be substituted by one or two $C_{1-3}$-alkyl groups, an amino group substituted by the group $R^{20}$ and a $C_{1-3}$-alkyl group wherein $R^{20}$ is as hereinbefore defined, while the groups mentioned for $R^{20}$ may each be substituted by one or two $C_{1-3}$-alkyl groups, an $R^{19}$—$C_{3-4}$-alkyl group wherein the $C_{3-4}$-alkyl moiety is straight-chained and may additionally be substituted by one or two $C_{1-3}$-alkyl groups, where $R^{19}$ is as hereinbefore defined, a 3-amino-2-oxopiperidin-5-yl or 3-amino-2-oxo-1-methylpiperidin-5-yl group, a pyrrolidin-3-yl, piperidin-3-yl, piperidin-4-yl, hexahydroazepin-3-yl, or hexahydroazepin-4-yl group which is substituted in the 1 position by an amino, $C_{1-3}$-alkylamino, or di-($C_{1-3}$-alkyl)amino group, or an azetidin-2-yl-$C_{1-2}$-alkyl, azetidin-3-yl-$C_{1-2}$-alkyl, pyrrolidin-2-yl-$C_{1-2}$-alkyl, pyrrolidin-3-yl, pyrrolidin-3-yl-$C_{1-2}$-alkyl, piperidin-2-yl-$C_{1-2}$-alkyl, piperidin-3-yl, piperidin-3-yl-$C_{1-2}$-alkyl, piperidin-4-yl, or piperidin-4-yl-$C_{1-2}$-alkyl group, while the abovementioned groups may each be substituted by one or two $C_{1-3}$-alkyl groups, wherein by the aryl groups mentioned in the definition of the above groups are meant phenyl or naphthyl groups, which may be mono- or disubstituted by $R_h$ independently of one another, where the substituents are identical or different and $R_h$ denotes a fluorine, chlorine, bromine, or iodine atom, a trifluoromethyl, cyano, nitro, amino, aminocarbonyl, aminosulfonyl, methylsulfonyl, acetylamino, methylsulfonylamino, $C_{1-3}$-alkyl, cyclopropyl, ethenyl, ethynyl, hydroxy, $C_{1-3}$-alkyloxy, difluoromethoxy, or trifluoromethoxy group, by the heteroaryl groups mentioned in the definitions of the abovementioned groups are meant a pyrrolyl, furanyl, thienyl, pyridyl, indolyl, benzofuranyl, benzothiophenyl, quinolinyl, or isoquinolinyl group, or a pyrrolyl, furanyl, thienyl, or pyridyl group wherein one or two methyne groups are replaced by nitrogen atoms, or an indolyl, benzofuranyl, benzothiophenyl, quinolinyl, or isoquinolinyl group wherein one to three methyne groups are replaced by nitrogen atoms, or a 1,2-dihydro-2-oxopyridinyl, 1,4-dihydro-4-oxopyridinyl, 2,3-dihydro-3-oxopyridazinyl, 1,2,3,6-tetrahydro-3,6-dioxopyridazinyl, 1,2-dihydro-2-oxopyrimidinyl, 3,4-dihydro-4-oxopyrimidinyl, 1,2,3,4-tetrahydro-2,4-dioxopyrimidinyl, 1,2-dihydro-2-oxopyrazinyl, 1,2,3,4-tetrahydro-2,3-dioxopyrazinyl, 2,3-dihydro-2-oxoindolyl, 2,3-dihydrobenzofuranyl, 2,3-dihydro-2-oxo-1H-benzimidazolyl, 2,3-dihydro-2-oxobenzoxazolyl, 1,2-dihydro-2-oxoquinolinyl, 1,4-dihydro-4-oxoquinolinyl, 1,2-dihydro-1-oxoisoquinolinyl, 1,4-dihydro-4-oxocinnolinyl, 1,2-dihydro-2-oxoquinazolinyl, 3,4-dihydro-4-oxoquinazolinyl, 1,2,3,4-tetrahydro-2,4-dioxoquinazolinyl, 1,2-dihydro-2-oxoquinoxalinyl, 1,2,3,4-tetrahydro-2,3-dioxoquinoxalinyl, 1,2-dihydro-1-oxophthalazinyl, 1,2,3,4-tetrahydro-1,4-dioxophthalazinyl, chromanyl, cumarinyl, 2,3-dihydrobenzo[1,4]dioxinyl, or 3,4-dihydro-3-oxo-2H-benzo[1,4]oxazinyl group, and the abovementioned heteroaryl groups may be mono- or disubstituted by $R_h$, while the substituents may be identical or different and $R_h$ is as hereinbefore defined, and, unless otherwise stated, the abovementioned alkyl, alkenyl, and alkynyl groups may be straight-chain or branched, the tautomers, enantiomers, diastereomers, the mixtures thereof, the prodrugs thereof, and the salts thereof.

Compounds which contain a group that can be cleaved in vivo are prodrugs of the corresponding compounds in which this group that can be cleaved in vivo has been cleaved.

The carboxy groups mentioned in the definition of the abovementioned groups may be replaced by a group which can be converted into a carboxy group in vivo or by a group which is negatively charged under physiological conditions. The amino and imino groups mentioned in the definition of the abovementioned groups may be substituted by a group which can be cleaved in vivo. Such groups are described for example in WO 98/46576 and by N. M. Nielsen et al. in International Journal of Pharmaceutics 39, 75-85 (1987).

By a group which can be converted in vivo into a carboxy group is meant, for example, a hydroxymethyl group, a carboxy group esterified with an alcohol wherein the alcohol moiety is preferably a $C_{1-6}$-alkanol, a phenyl-$C_{1-3}$-alkanol, or a $C_{3-9}$-cycloalkanol, while a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkyloxycarbonyl, or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol, or phenyl-$C_{3-5}$-alkynol with the proviso that no bonds to the oxygen atom start from a carbon atom which carries a double or triple bond, a $C_{3-8}$-cycloalkyl-$C_{1-3}$-alkanol, or a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol, or an alcohol of formula

wherein:

$R_p$ denotes a $C_{1-8}$-alkyl, $C_{5-7}$-cycloalkyl, $C_{1-8}$-alkyloxy, $C_{5-7}$-cycloalkyloxy, phenyl, or phenyl-$C_{1-3}$-alkyl group, $R_q$ denotes a hydrogen atom, a $C_{1-3}$-alkyl, $C_{5-7}$-cycloalkyl, or phenyl group and $R_r$ denotes a hydrogen atom or a $C_{1-3}$-alkyl group, by a group which is negatively charged under physiological conditions is meant, for example, a tetrazol-5-yl, phenylcarbonylaminocarbonyl, trifluoromethylcarbonylaminocarbonyl, $C_{1-6}$-alkylsulfonylamino, phenylsulfonylamino, benzylsulfonylamino, trifluoromethylsulfonylamino, $C_{1-6}$-alkylsulfonylaminocarbonyl, phenylsulfonylaminocarbonyl, benzylsulfonylaminocarbonyl, or perfluoro-$C_{1-6}$-alkylsulfonylaminocarbonyl group and by a group which can be cleaved in vivo from an imino or amino group is meant, for example, a hydroxy group, an acyl group such as a phenylcarbonyl group optionally mono- or disubstituted by fluorine, chlorine, bromine, or iodine atoms, by $C_{1-3}$-alkyl or $C_{1-3}$-alkyloxy groups, while the substituents may be identical or different, a pyridinoyl group or a $C_{1-6}$-alkanoyl group such as a formyl, acetyl, propionyl, butanoyl, pentanoyl, or hexanoyl group, a 3,3,3-trichloropropionyl or allyloxycarbonyl group, a $C_{1-6}$-alkyloxycarbonyl or $C_{1-6}$-alkylcarbonyloxy group, wherein hydrogen atoms may be wholly or partially replaced by fluorine or chlorine atoms such as the methoxycarbonyl, ethoxycarbonyl, propoxycarbonyl, isopropoxycarbonyl, butoxycarbonyl, tert-butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert-butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy, or hexadecylcarbonyloxy group, a phenyl-$C_{1-6}$-alkyloxycarbonyl group such as a benzyloxycarbonyl, phenylethoxycarbonyl, or phenylpropoxycarbonyl group, a 3-aminopropionyl group wherein the amino group may be mono- or disubstituted by $C_{1-6}$-alkyl or $C_{3-7}$-cycloalkyl groups and the substituents may be identical or different, a $C_{1-3}$-alkylsulfonyl-$C_{2-4}$-alkyloxycarbonyl, $C_{1-3}$-alkyloxy-$C_{2-4}$-alkyloxy-$C_{2-4}$-alkyloxycarbonyl, $R_p$—CO—O—($R_qCR_r$)—O—CO, $C_{1-6}$-alkyl-CO—NH—($R_sCR_t$)—O—CO—, or $C_{1-6}$-alkyl-CO—O—($R_sCR_t$)—($R_sCR_t$)—O—CO— group, wherein $R_p$ to $R_r$ are as hereinbefore defined, and $R_s$ and $R_t$, which may be identical or different, denote hydrogen atoms or $C_{1-3}$-alkyl groups.

Moreover, the saturated alkyl and alkyloxy moieties which contain more than 2 carbon atoms mentioned in the foregoing definitions and those that follow, unless otherwise stated, also include the branched isomers thereof such as, for example, an isopropyl, tert-butyl, isobutyl group, etc.

Preferred compounds of general formula (I) are those wherein
$R^1$, $R^2$, and $R^3$ are as hereinbefore defined, and
$R^4$ denotes a pyrrolidin-1-yl group which is substituted in the 3 position by an amino group,
a piperidin-1-yl group which is substituted in the 3 position by an amino group,
a hexahydroazepin-1-yl group which is substituted in the 3 position or 4 position by an amino group,
a (2-aminocyclohexyl)amino group,
a cyclohexyl group which is substituted in the 3 position by an amino group, or
an N-(2-aminoethyl)methylamino or an N-(2-aminoethyl)ethylamino group,
wherein, unless otherwise stated, the abovementioned alkyl, alkenyl, and alkynyl groups may be straight-chain or branched,
the tautomers, enantiomers, diastereomers, the mixtures thereof, and salts thereof.

Particularly preferred compounds of general formula (I) are those wherein:
$R^1$ denotes a phenylcarbonylmethyl group wherein the phenyl moiety is substituted by $R^{10}$, wherein
$R^{10}$ denotes a formylamino group,
a $C_{3-7}$-cycloalkyl-carbonylamino or $C_{3-7}$-cycloalkyl-$C_{1-3}$-alkyl-carbonylamino group,
a $C_{6-9}$-bicycloalkyl-carbonylamino group,
a $C_{5-7}$-cycloalkyl-carbonylamino group wherein a methylene group is replaced by an oxygen or sulfur atom or by an imino, sulfinyl, or sulfonyl group,
a (1,3-dioxolanyl)carbonylamino, (1,4-dioxanyl)carbonylamino, morpholin-2-ylcarbonylamino, morpholin-3-ylcarbonylamino, or piperazin-2-ylcarbonylamino group,
a $C_{5-7}$-cycloalkyl-carbonylamino group wherein a —CH$_2$—CH$_2$ group is replaced by an —NH—CO group,
a $C_{5-7}$-cycloalkyl-carbonylamino group wherein a —CH$_2$—CH$_2$—CH$_2$ group is replaced by an —NH—CO—O group,
a $C_{5-7}$-cycloalkyl-carbonylamino group wherein a methylene group is replaced by a carbonyl group,
a $C_{5-7}$-cycloalkenyl-carbonylamino or $C_{5-7}$-cycloalkenyl-$C_{1-3}$-alkyl-carbonylamino group,
a $C_{3-7}$-cycloalkyl-sulfonylamino, phenylsulfonylamino, or phenyl-$C_{1-3}$-alkyl-sulfonylamino group or
a pyridinylcarbonylamino group;
$R^2$ denotes a hydrogen atom or a $C_{1-3}$-alkyl group;
$R^3$ denotes a $C_{4-6}$-alkenyl, a 2-butyn-1-yl, or a 1-cyclopenten-1-ylmethyl group; and
$R^4$ denotes a piperidin-1-yl group which is substituted in the 3 position by an amino group,
a hexahydroazepin-1-yl group which is substituted in the 3 position or 4 position by an amino group,
a (2-aminocyclohexyl)amino group,
a cyclohexyl group which is substituted in the 3 position by an amino group, or
an N-(2-aminoethyl)methylamino or an N-(2-aminoethyl)ethylamino group,
wherein, unless otherwise stated, the abovementioned alkyl, alkenyl, and alkynyl groups may be straight-chain or branched,
the tautomers, enantiomers, diastereomers, the mixtures thereof and the salts thereof.

Most particularly preferred compounds of general formula (I) are those wherein $R^1$ denotes a phenylcarbonylmethyl group wherein the phenyl moiety is substituted by a formylamino, pyridinylcarbonylamino, or cyclopropylcarbonylamino group;
$R^2$ denotes a methyl group;
$R^3$ denotes a 2-buten-1-yl, 3-methyl-2-buten-1-yl, or a 2-butyn-1-yl group; and
$R^4$ denotes a (3-aminopiperidin-1-yl) group,
the tautomers, enantiomers, diastereomers, the mixtures thereof, and the salts thereof,
but particularly those compounds of general formula (I) wherein:
$R^1$ denotes a [2-(cyclopropylcarbonylamino)phenyl]carbonylmethyl or [2-(pyridylcarbonylamino)phenyl]carbonylmethyl group;
$R^2$ denotes a methyl group;
$R^3$ denotes a 2-buten-1-yl, 3-methyl-2-buten-1-yl, or a 2-butyn-1-yl group; and
$R^4$ denotes a (3-aminopiperidin-1-yl) group,
the tautomers, enantiomers, diastereomers, the mixtures thereof, and the salts thereof.

The following compounds of general formula (I) are particularly preferred:
(1) 1-[2-(2-formylaminophenyl)-2-oxoethyl]3-methyl-7-(3-methyl-2-buten-1-yl)-8-(3-aminopiperidin-1-yl)xanthine;
(2) 1-(2-{2-[(cyclopropylcarbonyl)amino]phenyl}-2-oxoethyl)-3-methyl-7-(3-methyl-2-buten-1-yl)-8-(3-aminopiperidin-1-yl)xanthine;
(3) 1-[2-(2-formylaminophenyl)-2-oxoethyl]3-methyl-7-(2-butyn-1-yl)-8-(3-aminopiperidin-1-yl)xanthine;
(4) 1-(2-{2-[(cyclopropylcarbonyl)amino]phenyl}-2-oxoethyl)-3-methyl-7-((E)-2-buten-1-yl)-8-((R)-3-aminopiperidin-1-yl)xanthine;
(5) 1-(2-{2-[(cyclopropylcarbonyl)amino]phenyl}-2-oxoethyl)-3-methyl-7-((E)-2-buten-1-yl)-8-((S)-3-aminopiperidin-1-yl)xanthine;
(6) 1-(2-{2-[(cyclopropylcarbonyl)amino]phenyl}-2-oxoethyl)-3-methyl-7-(2-butyn-1-yl)-8-((R)-3-aminopiperidin-1-yl)xanthine;
(7) 1-(2-{2-[(cyclopropylcarbonyl)amino]phenyl}-2-oxoethyl)-3-methyl-7-(2-butyn-1-yl)-8-((S)-3-aminopiperidin-1-yl)xanthine; and
(8) 1-[2-(2-{[(pyridin-2-yl)carbonyl]amino}phenyl)-2-oxoethyl]3-methyl-7-((E)-2-buten-1-yl)-8-(3-aminopiperidin-1-yl)xanthine, as well as the tautomers, enantiomers, diastereomers, the mixtures thereof, and the salts thereof.

According to the invention, the compounds of general formula (I) are obtained by methods known per se, for example, by the following methods:
(a) In order to prepare compounds of general formula (I) wherein $R^4$ is one of the abovementioned groups linked to the xanthine skeleton via a nitrogen atom:
reacting a compound of general formula (II)

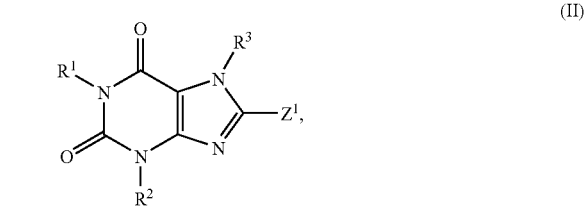

wherein $R^1$, $R^2$, and $R^3$ are as hereinbefore defined and $Z^1$ denotes a leaving group such as a halogen atom, a substituted hydroxy, mercapto, sulfinyl, sulfonyl, or sulfonyloxy group, such as, for example, a chlorine or bromine atom, or a methanesulfonyl or methanesulfonyloxy group, with an amine of general formula $R^{4'}$—H, wherein $R^{4'}$ denotes one of the groups mentioned hereinbefore for $R^4$ which is linked to the xanthine skeleton via a nitrogen atom.

The reaction is expediently carried out in a solvent such as isopropanol, butanol, tetrahydrofuran, dioxane, dimethylformamide, dimethylsulfoxide, ethylene glycol monomethylether, ethylene glycol diethylether, or sulfolane, optionally in the presence of an inorganic or tertiary organic base, e.g., sodium carbonate, potassium carbonate, or potassium hydroxide, a tertiary organic base, e.g., triethylamine, or in the presence of N-ethyldiisopropylamine (Hünig base), while these organic bases may simultaneously also serve as solvent, and optionally in the presence of a reaction accelerator such as an alkali metal halide or a palladium-based catalyst at temperatures between −20° C. and 180° C., but preferably at temperatures between −10° C. and 120° C. The reaction may, however, also be carried out without a solvent or in an excess of the amine of general formula $R^{4'}$—H.

(b) Deprotecting a compound of general formula (III)

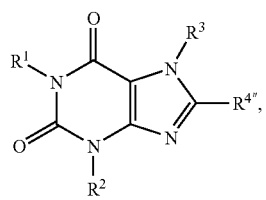

(III)

wherein $R^1$, $R^2$, and $R^3$ are as hereinbefore defined and $R^{4''}$ denotes one of the groups mentioned for $R^4$ hereinbefore which contain an imino, amino, or alkylamino group, while the imino, amino, or alkylamino group is substituted by a protective group, optionally followed by subsequent alkylation of the imino, amino, or $C_{1-3}$-alkylamino group.

The liberating of an amino group from a protected precursor is a standard reaction in synthetic organic chemistry. There are many examples of suitable protective groups. A summary of the chemistry of protective groups can be found in Theodora W. Greene and Peter G. M. Wuts, *Protective Groups in Organic Synthesis*, Second Edition, 1991, published by John Wiley and Sons, and in Philip J. Kocienski, *Protecting Groups*, published by Georg Thieme, 1994.

The following are examples of protective groups:

the tert-butyloxycarbonyl group which can be cleaved by treating with an acid such as, for example, trifluoroacetic acid or hydrochloric acid or by treating with bromotrimethylsilane or iodotrimethylsilane, optionally using a solvent such as methylene chloride, ethyl acetate, dioxane, methanol, isopropanol, or diethylether at temperatures between 0° C. and 80° C., the 2,2,2-trichloroethoxycarbonyl group which can be cleaved by treating with metals such as, for example, zinc or cadmium in a solvent such as acetic acid or a mixture of tetrahydrofuran and a weak aqueous acid at temperatures between 0° C. and the boiling temperature of the solvent used, and the carbobenzyloxycarbonyl group which can be cleaved, for example, by hydrogenolysis in the presence of a noble metal catalyst such as, for example, palladium-charcoal and a solvent such as for example alcohols, ethyl acetate, dioxane, tetrahydrofuran, or mixtures of these solvents at temperatures between 0° C. and the boiling point of the solvent, by treating with boron tribromide in methylene chloride at temperatures between −20° C. and ambient temperature, or by treating with aluminum chloride/anisole at temperatures between 0° C. and ambient temperature.

The optional subsequent introduction of a $C_{1-3}$-alkyl group may be done by alkylation or reductive alkylation.

The subsequent alkylation is optionally carried out in a solvent or mixture of solvents such as methylene chloride, dimethylformamide, benzene, toluene, chlorobenzene, tetrahydrofuran, benzene/tetrahydrofuran, or dioxane with an alkylating agent such as a corresponding halide or sulfonic acid ester, e.g., with methyl iodide, ethyl bromide, or dimethyl sulfate, optionally in the presence of a tertiary organic base or in the presence of an inorganic base, conveniently at temperatures between 0° C. and 150° C., preferably at temperatures between 0° C. and 100° C.

The subsequent reductive alkylation is carried out with a corresponding carbonyl compound such as formaldehyde, acetaldehyde, propionaldehyde, or acetone in the presence of a complex metal hydride such as sodium borohydride, lithium borohydride, sodium triacetoxyborohydride, or sodium cyanoborohydride, conveniently at a pH of 6-7 and at ambient temperature or in the presence of a hydrogenation catalyst, e.g., with hydrogen in the presence of palladium/charcoal, under a hydrogen pressure of 1 bar to 5 bar. The methylation may also be carried out in the presence of formic acid as reducing agent at elevated temperatures, e.g., at temperatures between 60° C. and 120° C.

In the reactions described hereinbefore, any reactive groups present such as carboxy, amino, alkylamino, or imino groups may be protected during the reaction by conventional protecting groups which are cleaved again after the reaction. For example, a protecting group for a carboxy group may be a trimethylsilyl, methyl, ethyl, tert-butyl, benzyl, or tetrahydropyranyl group, and protecting groups for an amino, alkylamino, or imino group may be a formyl, acetyl, trifluoroacetyl, ethoxycarbonyl, tert-butoxycarbonyl, benzyloxycarbonyl, benzyl, methoxybenzyl, or 2,4-dimethoxybenzyl group and additionally, for the amino group, a phthalyl group.

Any protecting group used is optionally subsequently cleaved, for example, by hydrolysis in an aqueous solvent, e.g., in water, isopropanol/water, acetic acid/water, tetrahydrofuran/water, or dioxane/water, in the presence of an acid such as trifluoroacetic acid, hydrochloric acid, or sulfuric acid or in the presence of an alkali metal base such as sodium hydroxide or potassium hydroxide or aprotically, e.g., in the presence of iodotrimethylsilane, at temperatures between 0° C. and 120° C., preferably at temperatures between 10° C. and 100° C.

However, a benzyl, methoxybenzyl, or benzyloxycarbonyl group is cleaved, for example, hydrogenolytically, e.g., with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0° C. and 100° C., but preferably at temperatures between 20° C. and 60° C., and at a hydrogen pressure of 1 bar to 7 bar, but preferably 3 bar to 5 bar. A 2,4-dimethoxybenzyl group, however, is preferably cleaved in trifluoroacetic acid in the presence of anisole.

A tert-butyl or tert-butyloxycarbonyl group is preferably cleaved by treating with an acid such as trifluoroacetic acid or hydrochloric acid or by treating with iodotrimethylsilane, optionally using a solvent such as methylene chloride, dioxane, methanol, or diethylether.

A trifluoroacetyl group is preferably cleaved by treating with an acid such as hydrochloric acid, optionally in the presence of a solvent such as acetic acid at temperatures between 50° C. and 120° C., or by treating with sodium hydroxide solution, optionally in the presence of a solvent such as tetrahydrofuran at temperatures between 0° C. and 50° C.

A phthalyl group is preferably cleaved in the presence of hydrazine or a primary amine such as methylamine, ethylamine, or n-butylamine in a solvent such as methanol, ethanol, isopropanol, toluene/water, or dioxane at temperatures between 20° C. and 50° C.

Moreover, the compounds of general formula (I) obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers. Thus, for example, the cis/trans mixtures may be resolved by chromatography into the cis and trans isomers thereof, the compounds of general formula (I) obtained which occur as racemates may be separated by methods known per se (cf N. L. Allinger and E. L. Eliel in "Topics in Stereochemistry", Vol. 6, Wiley Interscience, 1971) into their optical antipodes and compounds of general formula (I) with at least 2 asymmetric carbon atoms may be resolved into their diastereomers on the basis of their physical-chemical differences using methods known per se, e.g., by chromatography and/or fractional crystallization, and, if these compounds are obtained in racemic form, they may subsequently be resolved into the enantiomers as mentioned above.

The enantiomers are preferably separated by column separation on chiral phases or by recrystallization from an optically active solvent or by reacting with an optically active substance which forms racemic salts or derivatives such as, e.g., esters or amides of an optically active substance, particularly acids and the activated derivatives or alcohols thereof, and separating the diastereomeric mixture of salts or derivatives thus obtained, e.g., on the basis of their differences in solubility, whilst the free antipodes may be released from the pure diastereomeric salts or derivatives by the action of suitable agents. Optically active acids in common use are, e.g., the D- and L-forms of tartaric acid or dibenzoyltartaric acid, di-o-tolyltartaric acid, malic acid, mandelic acid, camphorsulfonic acid, glutamic acid, aspartic acid, or quinic acid. An optically active alcohol may be, for example, (+) or (−)-menthol and an optically active acyl group in amides, for example, may be a (+)- or (−)-menthyloxycarbonyl.

Furthermore, the compounds of formula (I) may be converted into the salts thereof, particularly for pharmaceutical use, into the physiologically acceptable salts with inorganic or organic acids. Acids which may be used for this purpose include, for example, hydrochloric acid, hydrobromic acid, sulfuric acid, methanesulfonic acid, phosphoric acid, fumaric acid, succinic acid, lactic acid, citric acid, tartaric acid, or maleic acid.

Moreover, if the new compounds of formula (I) thus obtained contain a carboxy group, they may subsequently, if desired, be converted into the salts thereof with inorganic or organic bases, particularly for pharmaceutical use into the physiologically acceptable salts thereof. Suitable bases for this purpose include, for example, sodium hydroxide, potassium hydroxide, arginine, cyclohexylamine, ethanolamine, diethanolamine, and triethanolamine.

The compounds of general formulae (II) and (III) used as starting materials are either known from the literature in some cases or may be obtained by methods known from the literature (cf Examples I to VII).

As already mentioned hereinbefore, the compounds of general formula (I) according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in a test set-up in which an extract of human colon carcinoma cell line Caco-2 is used as the DPP-IV source. The differentiation of the cells in order to induce the DPP-IV expression was carried out as described by Reiher et al., "Increased Expression of Intestinal Cell Line Caco-2", Proc. Natl. Acad. Sci. Vol. 90, pages 5757-5761 (1993). The cell extract was obtained from cells solubilized in a buffer (10 mM Tris HCl, 0.15 M NaCl, 0.04 t.i.u. aprotinin, 0.5% Nonidet P-40, pH 8.0) by centrifuging at 35,000 g for 30 minutes at 4° C. (to remove cell debris).

The DPP-IV assay was carried out as follows:

50 µL substrate solution (AFC; AFC is amido-4-trifluoromethylcoumarin), final concentration 100 µM, were placed in black microtitre plates. 20 µL of assay buffer (final concentrations 50 mM Tris HCl pH 7.8, 50 mM NaCl, 1% DMSO) was pipetted in. The reaction was started by adding 30 µL of solubilized Caco-2 protein (final concentration 0.14 µg of protein per well). The test substances to be investigated were typically added prediluted in 20 µL, and the volume of assay buffer was then reduced accordingly. The reaction was carried out at ambient temperature, incubating for 60 minutes. Then the fluorescence was measured in a Victor 1420 Multilabel Counter, the excitation wavelength being 405 nm and the emission wavelength being 535 nm. Blank readings (corresponding to 0% activity) were obtained in mixtures without any Caco-2 protein (volume replaced by assay buffer), control values (corresponding to 100% activity) were obtained in mixtures with no substance added. The potency of the test substances in question, expressed as $IC_{50}$ values, was calculated from dosage/activity curves consisting of 11 measuring points in each case. The following results were obtained:

| Compound (Example No.) | DPP-IV inhibition $IC_{50}$[nM] |
|---|---|
| 1 | 5 |
| 1(1) | 11 |
| 1(2) | 3 |
| 1(3) | 4 |
| 1(4) | 3 |
| 1(5) | 3 |
| 1(6) | 5 |
| 1(7) | 8 |

The compounds prepared according to the invention are well tolerated, as, for example, when 10 mg/kg of the compound of Example 1(5) were administered to rats by oral route, no changes in the animals' behavior could be detected.

In view of their ability to inhibit DPP-IV activity, the compounds of general formula (I) according to the invention and the corresponding pharmaceutically acceptable salts thereof are suitable for treating all those conditions or illnesses which can be influenced by the inhibition of the DPP-IV activity. It is therefore to be expected that the compounds according to the invention will be suitable for the prevention or treatment of diseases or conditions such as type 1 and type 2 diabetes mellitus, diabetic complications (such as, e.g., retinopathy, nephropathy, or neuropathies), metabolic acidosis or ketosis, reactive hypoglycemia, insulin resistance, metabolic syndrome, dyslipidemias of various origins, arthritis, atherosclerosis and related diseases, obesity, allograft transplantation and calcitonin-induced osteoporosis. In addition, these substances are capable of preventing B-cell degeneration such as, e.g., apoptosis or necrosis of pancreatic B-cells. The substances are also suitable for improving or restoring the function of pancreatic cells and also increasing the number and size of pancreatic B-cells. Additionally, and on the basis of the role of the Glucagon-Like Peptides, such as, e.g., GLP-1 and GLP-2, and their link with DPP-IV inhibition, it is likely that the compounds according to the invention are suitable for achieving, inter alia, a sedative or anxiety-relieving effect and also of favorably affecting catabolic states after operations or hormonal stress responses or of reducing mortality or morbidity after myocardial infarct. They are also suitable for treating all conditions which are connected with the abovementioned effects and which are mediated by GLP-1 or GLP-2. The compounds according to the invention may also be used as diuretics or antihypertensives and are suitable for preventing and treating acute renal failure. Furthermore, the compounds according to the invention may be used to treat inflammatory diseases of the respiratory tract. They are also suitable for the prevention and treatment of chronic inflammatory intestinal diseases such as, e.g., irritable bowel syndrome (IBS), Crohn disease, or ulcerative colitis and also pancreatitis. It is also likely that they can be used for all kinds of damage to or impairment of the gastrointestinal tract such as colitis and enteritis, for example. It is also expected that DPP-IV inhibitors and hence also the compounds according to the invention may be used to treat infertility or to improve fertility in humans or mammals, particularly when the infertility is connected with insulin resistance or polycystic ovary syndrome. On the other hand, these substances are suitable for affecting sperm motility and can thus be used as male contraceptives. The substances are also suitable for treating deficiencies of growth hormone which are associated with reduced stature, and may also be used to advantage in any indications in which growth hormone may be used. The compounds according to the invention are also suitable, on the basis of their inhibitory effect on DPP-IV, for treating various autoimmune diseases such as, e.g., rheumatoid arthritis, multiple sclerosis, thyroiditis, and Basedow disease, etc. They may also be used to treat viral diseases and also, for example, in HIV infections, for stimulating blood production, in benign prostatic hyperplasia, gingivitis, as well as for the treatment of neuronal defects and neurodegenerative diseases such as Alzheimer's disease, for example. The compounds described may also be used for the treatment of tumors, particularly for modifying tumor invasion and also metastasization; examples here are their use in treating T-cell lymphomas, acute lymphoblastic leukemia, cell-based pancreatic carcinomas, basal cell carcinomas, or breast cancers. Other indications are stroke, ischaemia of various origins, Parkinson disease and migraine. In addition, further indications include follicular and epidermal hyperkeratoses, increased keratinocyte proliferation, psoriasis, encephalomyelitis, glomerulonephritis, and lipodystrophies, as well as psychosomatic, depressive, and neuropsychiatric diseases of all kinds.

The compounds according to the invention may also be used in conjunction with other active substances. Therapeutic agents which are suitable for such combinations include, for example, antidiabetics, such as metformin, sulfonylureas (e.g., glibenclamide, tolbutamide, glimepiride), nateglinide, repaglinide, thiazolidinedione (e.g., rosiglitazone, pioglitazone), PPAR-gamma agonists (e.g., GI 262570) and antagonists, PPAR-gamma/alpha modulators (e.g., KRP 297), alpha-glucosidase inhibitors (e.g., acarbose or voglibose), other DPP-IV inhibitors, α2 antagonists, insulin and insulin analogues, GLP-1 and GLP-1 analogues (e.g., exendin-4) or amylin. Also, SGLT2 inhibitors such as T-1095, inhibitors of protein tyrosine phosphatase 1, substances which influence deregulated glucose production in the liver such as, e.g., inhibitors of glucose-6-phosphatase, or fructose-1,6-bisphosphatase, glycogen phosphorylase, glucagon receptor antagonists, and inhibitors of phosphoenol pyruvate carboxykinase, glycogen synthase kinase, or pyruvate dehydrokinase, lipid lowering agents, such as HMG-CoA-reductase inhibitors (e.g., simvastatin or atorvastatin), fibrates (e.g., bezafibrate or fenofibrate), nicotinic acid and its derivatives, PPAR-alpha agonists, PPAR-delta agonists, ACAT inhibitors (e.g., avasimibe) or cholesterol resorption inhibitors such as, for example, ezetimibe, bile acid-binding substances such as for example cholestyramine, inhibitors of ileac bile acid transport, HDL-raising compounds such as for example inhibitors of CETP or regulators of ABC1 or active substances for the treatment of obesity, such as, e.g., sibutramine or tetrahydrolipostatin, dexfenfluramine, axokine, antagonists of the cannabinoid-1 receptor, MCH-1 receptor antagonists, MC4 receptor agonists, NPY5 or NPY2 antagonists, or $\beta_3$-agonists such as SB-418790 or AD-9677, as well as agonists of the 5HT2c receptor.

It is also possible to combine the compounds with drugs for treating high blood pressure such as, e.g., AII antagonists or ACE inhibitors, diuretics, β-blockers, Ca-antagonists, etc., or combinations thereof.

The dosage required to achieve such an effect is expediently, by intravenous route, 1 mg to 100 mg, preferably 1 mg to 30 mg, and by oral route 1 mg to 1000 mg, preferably 1 mg to 100 mg, in each case 1 to 4 a day. For this purpose, the compounds of formula (I) prepared according to the invention, optionally combined with other active substances, may be incorporated together with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose, or fatty substances such as hard fat, or suitable mixtures thereof into conventional galenic preparations such as plain or coated tablets, capsules, powders, suspensions, or suppositories.

The Examples that follow are intended to illustrate the invention.

Preparation of the starting compounds:

EXAMPLE I

1-[2-(2-formylaminophenyl)-2-oxoethyl]-3-methyl-7-(3-methyl-2-buten-1-yl)-8-[3-(tert-butyloxycarbonylamino)piperidin-1-yl]xanthine A mixture of 1.2 mL of formic acid and 2 mL of acetic acid anhydride is heated to 60° C. for 10 minutes. 1 mL of this mixture is then added to 226 mg of 1-[2-(2-aminophenyl)-2-oxoethyl]-3-methyl-7-(3-methyl-2-buten-1-yl)-8-[3-(tertbutyloxycarbonyl-amino)piperidin-1-yl]xanthine and the reaction mixture is stirred for 15 minutes at 80° C. For working up, the reaction mixture is combined with methylene chloride and slowly made alkaline with saturated potassium carbonate solution. The aqueous phase is extracted with methylene chloride and the combined organic phases are dried over sodium sulfate and evaporated down. The crude product is further reacted without any further purification. Yield: 186 mg (78% of theory); $R_f$ value: 0.40 (silica gel, cyclohexane/ethyl acetate (3:7)); mass spectrum (ESI$^+$): m/z=594 [M+H]$^+$.

The following compound is obtained analogously to Example I:

1-[2-(2-formylaminophenyl)-2-oxoethyl]-3-methyl-7-(2-butyn-1-yl)-8-[3-(tert-butyloxycarbonylamino)piperidin-1-yl]xanthine $R_f$ value: 0.23 (silica gel, cyclohexane/ethyl acetate (3:7)); mass spectrum (ESI$^+$): m/z=578 [M+H]$^+$.

EXAMPLE II

1-[2-(2-aminophenyl)-2-oxoethyl]-3-methyl-7-(3-methyl-2-buten-1-yl)-8-3-(tert-butyloxycarbonylamino)piperidin-1-yl]xanthine Prepared by treating 1-[2-(2-nitrophenyl)-2-oxoethyl]-3-methyl-7-(3-methyl-2-buten-1-yl)-8-[3-(tert-butyloxycarbonylamino)piperidin-1-yl]xanthine with powdered iron in a mixture of ethanol, water, and glacial acetic acid (150:50:14) at 90° C. Mass spectrum (ESI$^+$): m/z=566 [M+H]$^+$.

The following compounds are obtained analogously to Example II:

(1) 1-[2-(2-aminophenyl)-2-oxoethyl]-3-methyl-7-(2-butyn-1-yl)-8-bromoxanthine

Mass spectrum (ESI$^+$): m/z=430, 432 [M+H]$^+$.

(2) 1-[2-(2-aminophenyl)-2-oxoethyl]-3-methyl-7-((E)-2-buten-1-yl)-8-[(R)-3-(tert-butyloxycarbonylamino)piperidin-1-yl]xanthine Mass spectrum (ESI$^+$): m/z=552 [M+H]$^+$.

(3) 1-[2-(2-aminophenyl)-2-oxoethyl]-3-methyl-7-((E)-2-buten-1-yl)-8-bromoxanthine $R_f$ value: 0.62 (silica gel, cyclohexane/ethyl acetate (4:6)); mass spectrum (ESI$^+$): m/z=432, 434 [M+H]$^+$.

EXAMPLE III

1-[2-(2-nitrophenyl)-2-oxoethyl]-3-methyl-7-(3-methyl-2-buten-1-yl)-8-[3-(tert-butyloxycarbonylamino)piperidin-1-yl]xanthine 2.20 g of 3-tert-butyloxycarbonylaminopiperidine is added at 65° C. to 4.40 g of 1-[2-(2-nitrophenyl)-2-oxoethyl]-3-methyl-7-(3-methyl-2-buten-1-yl)-8-chloroxanthine and 1.30 g of sodium carbonate in 50 mL of dimethylsulfoxide. The reaction mixture is stirred for approximately 16 hours at 65° C. After cooling to ambient temperature, it is poured onto a mixture of 600 mL of water and 100 g of ice. The precipitate formed is suction filtered and washed with water. The filter cake is dissolved in diethyl ether, and the solution is dried and evaporated down. The brown resinous flask residue is brought to crystallization with diisopropylether. Yield: 3.30 g (54% of theory); $R_f$ value: 0.52 (silica gel, cyclohexane/ethyl acetate (3:7)); mass spectrum (ESI$^+$): m/z=596 [M+H]$^+$.

The following compounds are obtained analogously to Example III:

(1) 1-[2-(2-aminophenyl)-2-oxoethyl]-3-methyl-7-(2-butyn-1-yl)-8-[3-(tert-butyloxy-carbonylamino)piperidin-1-yl]xanthine $R_f$ value: 0.50 (silica gel, methylene chloride/methanol (95:5)); mass spectrum (ESI$^+$): m/z=550 [M+H]$^+$.

(2) 1-[2-(2-nitrophenyl)-2-oxoethyl]-3-methyl-7-((E)-2-buten-1-yl)-8-[(R)-3-(tert-butyloxycarbonylamino)piperidin-1-yl]xanthine $R_f$ value: 0.50 (silica gel, cyclohexane/ethyl acetate (1:2)).

(3) 1-[2-(2-aminophenyl)-2-oxoethyl]-3-methyl-7-((E)-2-buten-1-yl)-8-[(S)-3-(tert-butyloxycarbonylamino)piperidin-1-yl]xanthine $R_f$ value: 0.40 (silica gel, cyclohexane/ethyl acetate=4:6); mass spectrum (ESI$^+$): m/z=552 [M+H]$^+$.

(4) 3-methyl-7-(2-butyn-1-yl)-8-[(R)-3-(tert-butyloxycarbonylamino)piperidin-1-yl]xanthine Melting point: 197° C.-200° C.; mass spectrum (ESI$^+$): m/z=417 [M+H]$^+$.

(5) 3-methyl-7-(2-butyn-1-yl)-8-[(S)-3-(tert-butyloxycarbonylamino)piperidin-1-yl]xanthine $R_f$ value: 0.52 (silica gel, ethyl acetate); mass spectrum (ESI$^+$): m/z=417 [M+H]$^+$.

(6) 1-[2-(2-aminophenyl)-2-oxoethyl]-3-methyl-7-((E)-2-buten-1-yl)-8-[3-(tert-butyloxycarbonylamino)piperidin-1-yl]xanthine $R_f$ value: 0.20 (silica gel, cyclohexane/ethyl acetate (1:1)); mass spectrum (ESI$^+$): m/z=552 [M+H]$^+$.

EXAMPLE IV

1-[2-(2-nitrophenyl)-2-oxoethyl]-3-methyl-7-(3-methyl-2-buten-1-yl)-8-chloroxanthine A mixture of 6.02 g of 3-methyl-7-(3-methyl-2-buten-1-yl)-8-chloroxanthine, 5.86 g of 2-bromo-1-(2-nitrophenyl)ethanone, and 5.00 g of potassium carbonate in 150 mL of N,N-dimethylformamide is stirred for approximately 26 hours at 60° C. For working up, the cooled reaction mixture is poured onto a mixture of 500 mL of 1 N sodium hydroxide solution and 200 g of ice. The precipitate formed is suction filtered and dried. Yield: 6.32 g (65% of theory); $R_f$ value: 0.50 (silica gel, cyclohexane/ethyl acetate (4:6)); mass spectrum (ESI$^+$): m/z=432, 434 [M+H]$^+$.

The following compounds are obtained analogously to Example IV:

(1) 1-[2-(2-nitrophenyl)-2-oxoethyl]-3-methyl-7-(2-butyn-1-yl)-8-bromoxanthine $R_f$ value: 0.77 (silica gel, methylene chloride/methanol (95:5)); mass spectrum (ESI$^+$): m/z=460, 462 [M+H]$^+$.

(2) 1-[2-(2-nitrophenyl)-2-oxoethyl]-3-methyl-7-((E)-2-buten-1-yl)-8-bromoxanthine $R_f$ value: 0.50 (silica gel, cyclohexane/ethyl acetate (1:1)); mass spectrum (ESI$^+$): m/z=462, 464 [M+H]$^+$.

(3) 1-[2-(2-nitrophenyl)-2-oxoethyl]-3-methyl-7-(2-butyn-1-yl)-8-[(R)-3-(tert-butyloxycarbonylamino)piperidin-1-yl]xanthine $R_f$ value: 0.60 (silica gel, methylene chloride/methanol (95:5)).

(4) 1-[2-(2-nitrophenyl)-2-oxoethyl]-3-methyl-7-(2-butyn-1-yl)-8-[(S)-3-(tert-butyloxycarbonylamino)piperidin-1-yl]xanthine $R_f$ value: 0.60 (silica gel, methylene chloride/methanol (95:5)); mass spectrum (ESI$^+$): m/z=580 [M+H]$^+$.

17

EXAMPLE V 3-methyl-7-(3-methyl-2-buten-1-yl)-8-chloroxanthine 5.87 mL of 1-bromo-3-methyl-2-butene is added to 10.56 g of 3-methyl-8-chloroxanthine and 17 mL of Hünig base in 100 mL of N,N-dimethylformamide. The reaction mixture is stirred for approximately 10 minutes at ambient temperature and then combined with 800 mL of water. The light-colored precipitate formed is suction filtered, washed with ethanol and diethyl ether and dried. Yield: 10.56 g (81% of theory); mass spectrum (ESI$^+$): m/z=269, 271 [M+H]$^+$.

The following compounds are obtained analogously to Example V:

(1) 3-methyl-7-(2-butyn-1-yl)-8-bromoxanthine
  $R_f$ value: 0.72 (silica gel, ethyl acetate); mass spectrum (ESI$^+$): m/z=297, 299 [M+H]$^+$.
(2) 3-methyl-7-((E)-2-buten-1-yl)-8-bromoxanthine
  Mass spectrum (ESI$^+$): m/z=299, 301 [M+H]$^+$.

EXAMPLE VI 1-(2-{2-[(cyclopropylcarbonyl)amino]phenyl}-2-oxoethyl)-3-methyl-7-(3-methyl-2-buten-1-yl)-8-8-[3-(tert-butyloxycarbonylaminopiperidin-1-yl]xanthine A mixture of 242 mg of 1-[2-(2-aminophenyl)-2-oxoethyl]-3-methyl-7-(3-methyl-2-buten-1-yl)-8-[3-(tert-butyloxycarbonylamino)piperidin-1-yl]xanthine and 44 µL of pyridine in N,N-dimethylformamide is combined with 39 µL of cyclopropanecarboxylic acid chloride and stirred for 2 hours at 80° C. Then another 20 µL of pyridine and 30 µL of cyclopropan-ecarboxylic acid chloride are added. After a further 10 hours at 80° C., the cooled reaction mixture is diluted with methylene chloride and combined with water. The aqueous phase is extracted with methylene chloride and the combined organic phases are evaporated down. The crude product is purified through a silica gel column with cyclohexane/ethyl acetate (7:3 to 4:6) as eluent. Yield: 90 mg (33% of theory); $R_f$ value: 0.60 (silica gel, cyclohexane/ethyl acetate (3:7)).

The following compounds are obtained analogously to Example VI:

(1) 1-(2-{2-[(cyclopropylcarbonyl)amino]phenyl}-2-oxoethyl)-3-methyl-7-((E)-2-buten-1-yl)-8-[(R)-3-(tert-butyloxycarbonylamino)piperidin-1-yl]xanthine
  $R_f$ value: 0.30 (silica gel, cyclohexane/ethyl acetate/isopropanol (8:1:1)); mass spectrum (ESI$^+$): m/z=620 [M+H]$^+$.
(2) 1-(2-{2-[(cyclopropylcarbonyl)amino]phenyl}-2-oxoethyl)-3-methyl-7-((E)-2-buten-1-yl)-8-[(S)-3-(tert-butyloxycarbonylamino)piperidin-1-yl]xanthine
  $R_f$ value: 0.53 (silica gel, cyclohexane/ethyl acetate/isopropanol (14:3:3)); mass spectrum (ESI$^+$): m/z=620 [M+H]$^+$.
(3) 1-(2-{2-[(cyclopropylcarbonyl)amino]phenyl}-2-oxoethyl)-3-methyl-7-(2-butyn-1-yl)-8-[(R)-3-(tert-butyloxycarbonylamino)piperidin-1-yl]xanthine
  $R_f$ value: 0.35 (silica gel, methylene chloride/methanol (95:5)); mass spectrum (ESI$^+$): m/z=618 [M+H]$^+$.
(4) 1-(2-{2-[(cyclopropylcarbonyl)amino]phenyl}-2-oxoethyl)-3-methyl-7-(2-butyn-1-yl)-8-[(S)-3-(tert-butyloxycarbonylamino)piperidin-1-yl]xanthine
  $R_f$ value: 0.35 (silica gel, methylene chloride/methanol (95:5)); mass spectrum (ESI$^+$): m/z=618 [M+H]$^+$.

18

(5) 1-[2-(2-{[(pyridin-2-yl)carbonyl]amino}phenyl)-2-oxoethyl]-3-methyl-7-((E)-2-buten-1-yl)-8-[3-(tert-butyloxycarbonylamino)piperidin-1-yl]xanthine
  $R_f$ value: 0.55 (silica gel, cyclohexane/ethyl acetate/isopropanol (14:3:3)); mass spectrum (ESI$^+$): m/z=657 [M+H]$^+$.

EXAMPLE VII

1-[2-(2-aminophenyl)-2-oxoethyl]-3-methyl-7-(2-butyn-1-yl)-8-[(R)-3-(tert-butyloxycarbonylamino)piperidin-1-yl]xanthine Prepared by reduction of 1-[2-(2-nitrophenyl)-2-oxoethyl]-3-methyl-7-(2-butyn-1-yl)-8-[(R)-3-(tert-butyloxycarbonylamino)piperidin-1-yl]xanthine with sodium dithionite in a mixture of methyl glycol and water (3:2) at 100° C. $R_f$ value: 0.50 (silica gel, cyclohexane/ethyl acetate (4:6)).

The following compound is obtained analogously to Example VII:

1-[2-(2-aminophenyl)-2-oxoethyl]-3-methyl-7-(2-butyn-1-yl)-8-[(S)-3-(tert-butyloxycarbonylamino)piperidin-1-yl]xanthine
  $R_f$ value: 0.34 (silica gel, methylene chloride/methanol (95:5)).

Preparation of the final compounds:

EXAMPLE 1

1-[2-(2-formylaminophenyl)-2-oxoethyl]-3-methyl-7-(3-methyl-2-buten-1-yl)-8-(3-aminopiperidin-1-yl)xanthine A solution of 180 mg of 1-[2-(2-formylaminophenyl)-2-oxoethyl]-3-methyl-7-(3-methyl-2-buten-1-yl)-8-[3-(tert-butyloxycarbonylamino)piperidin-1-yl]xanthine in 4 mL of methylene chloride is combined with 1 mL of trifluoroacetic acid and stirred for half an hour at ambient temperature. For working up, the reaction mixture is made slightly alkaline with 1 N sodium hydroxide solution and the aqueous phase is extracted with methylene chloride. The combined organic phases are evaporated down and purified through a silica gel column. Yield: 130 mg (87% of theory); $R_f$ value: 0.38 (Ready-made reversed phase TLC plate (E. Merck), acetonitrile/water/trifluoroacetic acid (100:100:0.1)); mass spectrum (ESI$^+$): m/z=494 [M+H]$^+$.

The following compounds are obtained analogously to Example 1:

(1) 1-(2-{2-[(cyclopropylcarbonyl)amino]phenyl}-2-oxoethyl)-3-methyl-7-(3-methyl-2-buten-1-yl)-8-(3-aminopiperidin-1-yl)xanthine
  $R_f$ value: 0.35 (Ready-made reversed phase TLC plate (E. Merck), acetonitrile/water/ trifluoroacetic acid (100:100:0.1)); mass spectrum (ESI$^+$): m/z=534 [M+H]$^+$.
(2) 1-[2-(2-formylaminophenyl)-2-oxoethyl]-3-methyl-7-(2-butyn-1-yl)-8-(3-aminopiperidin-1-yl)xanthine
  $R_f$ value: 0.20 (silica gel, methylene chloride/methanol/ conc. aqueous ammonia (90:10:1)); mass spectrum (ESI$^+$): m/z=478 [M+H]$^+$.
(3) 1-(2-{2-[(cyclopropylcarbonyl)amino]phenyl}-2-oxoethyl)-3-methyl-7-((E)-2-1-yl)-8-((R)-3-aminopiperidin-1-yl)xanthine
  $R_f$ value: 0.50 (Ready-made reversed phase TLC plate (E. Merck), acetonitrile/water/trifluoroacetic acid (50:50:0.1)); mass spectrum (ESI$^+$): m/z=520 [M+H]$^+$.

(4) 1-(2-{2-[(cyclopropylcarbonyl)amino]phenyl}-2-oxoethyl)-3-methyl-7-((E)-2-buten-1-yl)-8-((S)-3-aminopiperidin-1-yl)xanthine $R_f$ value: 0.50 (Ready-made reversed phase TLC plate (E. Merck), acetonitrile/water/trifluoroacetic acid (50:50:0.1)); mass spectrum (ESI$^+$): m/z=520 [M+H]$^+$.

(5) 1-(2-{2-[(cyclopropylcarbonyl)amino]phenyl}-2-oxoethyl)-3-methyl-7-(2-butyn-1-yl)-8-((R)-3-aminopiperidin-1-yl)xanthine Mass spectrum (ESI$^+$): m/z=518 [M+H]$^+$.

(6) 1-(2-{2-[(cyclopropylcarbonyl)amino]phenyl}-2-oxoethyl)-3-methyl-7-(2-butyn-1-yl)-8-((S)-3-aminopiperidin-1-yl)xanthine $R_f$ value: 0.14 (silica gel, methylene chloride/methanol/conc. aqueous ammonia (90:10:1)); mass spectrum (ESI$^+$): m/z=518 [M+H]$^+$.

(7) 1-[2-(2-{[(pyridin-2-yl)carbonyl]amino}phenyl)-2-oxoethyl]-3-methyl-7-((E)-2-buten-1-yl)-8-(3-aminopiperidin-1-yl)xanthine Mass spectrum (ESI$^+$): m/z=557 [M+H]$^+$.

The following compounds may also be obtained analogously to the foregoing Examples and other methods known from the literature:

(1) 1-(2-{2-[(cyclobutylcarbonyl)amino]phenyl}-2-oxoethyl)-3-methyl-7-(3-methyl-2-buten-1-yl)-8-(3-aminopiperidin-1-yl)xanthine;

(2) 1-(2-{2-[(cyclopentylcarbonyl)amino]phenyl}-2-oxoethyl)-3-methyl-7-(3-methyl-2-buten-1-yl)-8-(3-aminopiperidin-1-yl)xanthine;

(3) 1-(2-{2-[(cyclohexylcarbonyl)amino]phenyl}-2-oxoethyl)-3-methyl-7-((E)-2-buten-1-yl)-8-(3-aminopiperidin-1-yl)xanthine;

(4) 1-(2-{2-[(cycloheptylcarbonyl)amino]phenyl}-2-oxoethyl)-3-methyl-7-(2-butyn-1-yl)-8-(3-aminopiperidin-1-yl)xanthine;

(5) 1-[2-(2-{[(bicyclo[2.2.1]heptan-1-yl)carbonyl]amino}phenyl)-2-oxoethyl]-3-methyl-7-(3-methyl-2-buten-1-yl)-8-(3-aminopiperidin-1-yl)xanthine;

(6) 1-[2-(2-{[(bicyclo[2.2.2]octan-1-yl)carbonyl]amino}phenyl)-2-oxoethyl]-3-methyl-7-((E)-2-buten-1-yl)-8-(3-aminopiperidin-1-yl)xanthine;

(7) 1-[2-(2-{[(1-cyclobuten-1-yl)carbonyl]amino}phenyl)-2-oxoethyl]-3-methyl-7-(3-methyl-2-buten-1-yl)-8-(3-aminopiperidin-1-yl)xanthine;

(8) 1-[2-(2-{[(1-cyclopenten-1-yl)carbonyl]amino}phenyl)-2-oxoethyl]-3-methyl-7-[(1-cyclopenten-1-yl)methyl]-8-(3-aminopiperidin-1-yl)xanthine;

(9) 1-[2-(2-{[(1-cyclohexen-1-yl)carbonyl]amino}phenyl)-2-oxoethyl]-3-methyl-7-((E)-2-buten-1-yl)-8-(3-aminopiperidin-1-yl)xanthine;

(10) 1-[2-(2-{[(2-oxocyclohexane-1-yl)carbonyl]amino}phenyl)-2-oxoethyl]-3-methyl-7-[(1-cyclopenten-1-yl)methyl]-8-(3-aminopiperidin-1-yl)xanthine;

(11) 1-[2-(2-{[(2,6-dioxocyclohexane-1-yl)carbonyl]amino}phenyl)-2-oxoethyl]-3-methyl-7-[(1-cyclopenten-1-yl)methyl]-8-(3-aminopiperidin-1-yl)xanthine;

(12) 1-[2-(2-{[(tetrahydrofuran-2-yl)carbonyl]amino}phenyl)-2-oxoethyl]-3-methyl-7-(3-methyl-2-buten-1-yl)-8-(3-aminopiperidin-1-yl)xanthine;

(13) 1-[2-(2-{[(tetrahydrofuran-3-yl)carbonyl]amino}phenyl)-2-oxoethyl]-3-methyl-7-(2-butyn-1-yl)-8-(3-aminopiperidin-1-yl)xanthine;

(14) 1-[2-(2-{[(tetrahydrothiophen-2-yl)carbonyl]amino}phenyl)-2-oxoethyl]-3-methyl-7-[(1-cyclopenten-1-yl)methyl]-8-(3-aminopiperidin-1-yl)xanthine;

(15) 1-[2-(2-{[(tetrahydrothiophen-3-yl)carbonyl]amino}phenyl)-2-oxoethyl]-3-methyl-7-(2-butyn-1-yl)-8-(3-aminopiperidin-1-yl)xanthine;

(16) 1-[2-(2-{[(1-oxotetrahydrothiophen-2-yl)carbonyl]amino}phenyl)-2-oxoethyl]-3-methyl-7-[(1-cyclopenten-1-yl)methyl]-8-(3-aminopiperidin-1-yl)xanthine;

(17) 1-[2-(2-{[(1,1-dioxotetrahydrothiophen-2-yl)carbonyl]amino}phenyl)-2-oxoethyl]-3-methyl-7-[(1-cyclopenten-1-yl)methyl]-8-(3-aminopiperidin-1-yl)xanthine;

(18) 1-[2-(2-{[(pyrrolidin-2-yl)carbonyl]amino}phenyl)-2-oxoethyl]-3-methyl-7-(2-butyn-1-yl)-8-(3-aminopiperidin-1-yl)xanthine;

(19) 1-[2-(2-{[(pyrrolidin-3-yl)carbonyl]amino}phenyl)-2-oxoethyl]-3-methyl-7-((E)-2-buten-1-yl)-8-(3-aminopiperidin-1-yl)xanthine;

(20) 1-[2-(2-{[(tetrahydropyran-2-yl)carbonyl]amino}phenyl)-2-oxoethyl]-3-methyl-7-(3-methyl-2-buten-1-yl)-8-(3-aminopiperidin-1-yl)xanthine;

(21) 1-[2-(2-{[([1,3]dioxolan-4-yl)carbonyl]amino}phenyl)-2-oxoethyl]-3-methyl-7-((E)-1-buten-1-yl)-8-(3-aminopiperidin-1-yl)xanthine;

(22) 1-[2-(2-{[([1,4]dioxane-2-yl)carbonyl]amino}phenyl)-2-oxoethyl]-3-methyl-7-(3-methyl-2-buten-1-yl)-8-(3-aminopiperidin-1-yl)xanthine;

(23) 1-[2-(2-{[(morpholin-2-yl)carbonyl]amino}phenyl)-2-oxoethyl]-3-methyl-7-((E)-2-buten-1-yl)-8-(3-aminopiperidin-1-yl)xanthine;

(24) 1-[2-(2-{[(piperazin-2-yl)carbonyl]amino}phenyl)-2-oxoethyl]-3-methyl-7-(3-methyl-2-buten-1-yl)-8-(3-aminopiperidin-1-yl)xanthine;

(25) 1-[2-(2-{[(5-oxopyrrolidin-2-yl)carbonyl]amino}phenyl)-2-oxoethyl]-3-methyl-7-[(1-cyclopenten-1-yl)methyl]-8-(3-aminopiperidin-1-yl)xanthine;

(26) 1-[2-(2-{[(6-oxopiperidin-2-yl)carbonyl]amino}phenyl)-2-oxoethyl]-3-methyl-7-(3-methyl-2-buten-1-yl)-8-(3-aminopiperidin-1-yl)xanthine;

(27) 1-[2-(2-{[(2-oxo-oxazolidin-4-yl)carbonyl]amino}phenyl)-2-oxoethyl]-3-methyl-7-((E)-1-buten-1-yl)-8-(3-aminopiperidin-1-yl)xanthine;

(28) 1-[2-(2-{[(cyclopropylmethyl)carbonyl]amino}phenyl)-2-oxoethyl]-3-methyl-7-(2-butyn-1-yl)-8-(3-aminopiperidin-1-yl)xanthine;

(29) 1-[2-(2-{[(pyridin-3-yl)carbonyl]amino}phenyl)-2-oxoethyl]-3-methyl-7-(2-butyn-1-yl)-8-(3-aminopiperidin-1-yl)xanthine;

(30) 1-(2-{2-[(cyclopropylsulfonyl)amino]phenyl}-2-oxoethyl)-3-methyl-7-(2-butyn-1-yl)-8-(3-aminopiperidin-1-yl)xanthine;

(31) 1-(2-{2-[(phenylsulfonyl)amino]phenyl}-2-oxoethyl)-3-methyl-7-(2-butyn-1-yl)-8-(3-aminopiperidin-1-yl)xanthine; and

(32) 1-(2-{2-[(benzylsulfonyl)amino]phenyl}-2-oxoethyl)-3-methyl-7-(2-butyn-1-yl)-8-(3-aminopiperidin-1-yl)xanthine.

EXAMPLE 2

Coated Tablets Containing 75 mg of Active Substance 1 tablet core contains:

| | |
|---|---|
| active substance | 75.0 mg |
| calcium phosphate | 93.0 mg |

-continued

| | |
|---|---|
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation

The active substance is mixed with calcium phosphate, corn starch, polyvinylpyrrolidone, hydroxypropylmethylcellulose, and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape. Weight of core: 230 mg; die: 9 mm, convex. The tablet cores thus produced are coated with a film consisting essentially of hydroxypropylmethylcellulose. The finished film-coated tablets are polished with beeswax. Weight of coated tablet: 245 mg.

EXAMPLE 3

Tablets Containing 100 mg of Active Substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation

The active substance, lactose, and starch are mixed together and uniformly moistened with an aqueous solution of the polyvinylpyrrolidone. After the moist composition has been screened (2.0 mm mesh size) and dried in a rack-type drier at 50° C., it is screened again (1.5 mm mesh size) and the lubricant is added. The finished mixture is compressed to form tablets. Weight of tablet: 220 mg; diameter: 10 mm, biplanar, facetted on both sides and notched on one side.

EXAMPLE 4

Tablets Containing 150 mg of Active Substance

Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation

The active substance mixed with lactose, corn starch, and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture. Weight of tablet: 300 mg; die: 10 mm, flat.

EXAMPLE 5

Hard Gelatine Capsules Containing 150 mg of Active Substance 1 capsule contains:

| | |
|---|---|
| active substance | 150.0 mg |
| corn starch (dried) | approx. 80.0 mg |
| lactose (powdered) | approx. 87.0 mg |
| magnesium stearate | 3.0 mg |
| | approx. 420.0 mg |

Preparation

The active substance is mixed with the excipients, passed through a screen with a mesh size of 0.75 mm, and homogeneously mixed using a suitable apparatus. The finished mixture is packed into size 1 hard gelatine capsules. Capsule filling: approx. 320 mg; capsule shell: size 1 hard gelatine capsule.

EXAMPLE 6

Suppositories Containing 150 mg of Active Substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation

After the suppository mass has been melted, the active substance is homogeneously distributed therein and the melt is poured into chilled moulds.

EXAMPLE 7

Suspension Containing 50 mg of Active Substance 100 mL of suspension contains:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |

-continued

| | |
|---|---|
| flavoring | 0.30 g |
| dist. water | to 100 mL |

Preparation

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution, and the flavoring have been added and dissolved, the suspension is evacuated with stirring to eliminate air. 5 mL of suspension contain 50 mg of active substance.

EXAMPLE 8

Ampoules Containing 10 mg Active Substance

Composition:

| | |
|---|---|
| active substance | 10.0 mg |
| 0.01 N hydrochloric acid | q.s. |
| double-distilled water | to 2.0 mL |

Preparation

The active substance is dissolved in the necessary amount of 0.01 N HCl, made isotonic with common salt, filtered sterile, and transferred into 2 mL ampoules.

EXAMPLE 9

Ampoules Containing 50 mg of Active Substance

Composition:

| | |
|---|---|
| active substance | 50.0 mg |
| 0.01 N hydrochloric acid | q.s. |
| double-distilled water | to 10.0 mL |

Preparation

The active substance is dissolved in the necessary amount of 0.01 N HCl, made isotonic with common salt, filtered sterile, and transferred into 10 mL ampoules.

We claim:

1. The compound of formula (I)

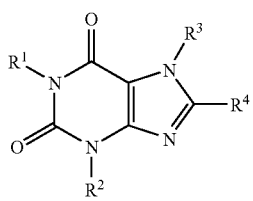

(1)

wherein:

$R^1$ is a [2-(cyclopropylcarbonylamino)phenyl]carbonylmethyl or [2-(pyridylcarbonyl-amino)phenyl]carbonylmethyl group;

$R^2$ is a methyl group;

$R^3$ is a 2-buten-1-yl, 3-methyl-2-buten-1-yl, or a 2-butyn-1-yl group; and $R^4$ is a (3-aminopiperidin-1-yl) group, or a prodrug or salt thereof.

2. A compound selected from:

(1) 1-(2-{2-[(cyclopropylcarbonyl)amino]phenyl}-2-oxoethyl)-3-methyl-7-(3-methyl-2-buten-1-yl)-8-(3-aminopiperidin-1-yl)xanthine;

(2) 1-(2-{2-[(cyclopropylcarbonyl)amino]phenyl}-2-oxoethyl)-3-methyl-7-((E)-2-buten-1-yl)-8-((R)-3-aminopiperidin-1-yl)xanthine;

(3) 1-(2-{2-[(cyclopropylcarbonyl)amino]phenyl}-2-oxoethyl)-3-methyl-7-((E)-2-buten-1-yl)-8-((S)-3-aminopiperidin-1-yl)xanthine;

(4) 1-(2-{2-[(cyclopropylcarbonyl)amino]phenyl}-2-oxoethyl)-3-methyl-7(-2-butyn-1-yl)-8-((R)-3-aminopiperidin-1-yl)xanthine;

(5) 1-(2-{2-[(cyclopropylcarbonyl)amino]phenyl}-2-oxoethyl)-3-methyl-7-(-2-butyn-1-yl)-8-((S)-3-aminopiperidin-1-yl)xanthine;

(6) 1-[2-(2-{[(pyridin-2-yl)carbonyl]amino }phenyl)-2-oxoethyl]-3-methyl-7-((E)-2-buten-1-yl)-8-(3-aminopiperidin- 1-yl)xanthine, or a prodrug or salt thereof.

3. The compound of formula (I) according to claim 1, wherein the compound is a physiologically acceptable salt.

4. The compound according to claim 2, wherein the compound is a physiologically acceptable salt.

5. A pharmaceutical composition comprising a compound of formula (I) according to claims 1 and an inert carrier or diluent.

6. The pharmaceutical composition according to claim 5, wherein the compound of formula (I) is incorporated with the inert carrier or diluent by mixing.

7. A method of treating type II diabetes mellitus, comprising administering to a patient in need thereof a pharmaceutically effective amount of a compound according to claim 1 or 2.

8. A method of treating or preventing type II diabetes mellitus or obesity, comprising administering to a patient in need thereof a pharmaceutically effective amount of a compound according to claim 1 or 2.

9. A pharmaceutical composition comprising a compound according to claim 2 and an inert carrier or diluent.

10. The pharmaceutical composition according to claim 9, wherein the compound is incorporated with the inert carrier or diluent by mixing.

* * * * *